US00PP18005P3

(12) United States Plant Patent
Jones, I et al.

(10) Patent No.: US PP18,005 P3
(45) Date of Patent: Sep. 11, 2007

(54) BERMUDA GRASS NAMED 'RJT'

(50) Latin Name: *Cynodon dactylon*
Varietal Denomination: RJT

(76) Inventors: Randall L. Jones, I, 13750 E. Levy St., Williston, FL (US) 32696; Randall L. Jones, II, 291 E. Country Club Dr., Williston, FL (US) 32696; Stewart T. Bennett, 14261 Clubhouse Dr., Bokeelia, FL (US) 33922

( * ) Notice: Subject to any disclaimer, the term of this patent is extended or adjusted under 35 U.S.C. 154(b) by 0 days.

(21) Appl. No.: 11/149,601

(22) Filed: Jun. 10, 2005

(65) Prior Publication Data

US 2006/0282930 P1 Dec. 14, 2006

(51) Int. Cl.
*A01H 5/00* (2006.01)

(52) U.S. Cl. ..... Plt./389

(58) Field of Classification Search ..... Plt./389
See application file for complete search history.

*Primary Examiner*—Kent Bell
*Assistant Examiner*—Annette H Para
(74) *Attorney, Agent, or Firm*—Laura G. Barrow

(57) ABSTRACT

A new and distinct cultivar of dwarf Bermuda grass, named RJT, is described and illustrated herein. The cultivar is characterized by its very fine texture when closely mown, the retention of its fine texture at higher heights of cut, its low nutrient needs, its very low thatching characteristics as compared to other dwarf Bermuda grasses, and its prolonged proven stability against mutation.

7 Drawing Sheets

SUMMARY OF INVENTION

The present invention relates to a new cultivar of dwarf-type Bermuda grass (*Cynodon dactylon*) that is particularly suited as a turf grass for southern U.S. golf course greens, tees, fairways, roughs, and other recreational sports turf facilities. The cultivar may also be used in other areas, including, but not limited to home lawns, parks, cemeteries, and the like. The new cultivar of the present invention is herein referred to by the name of RJT.

The RJT cultivar is a very dwarf leaf-bladed, low-growing (by nature) Bermuda grass spreading by rhizomes and stolons. The grass also maintains a good appearance when allowed to grow to taller heights. RJT is especially well suited for use on golf course greens, bowling greens, or grassed tennis courts that desire an extreme low cutting height ranging from 0.125" to 0.095". The cultivar is also suitable for use in any turf-use area where a superior dwarf Bermuda grass is desired. Extended research has also shown that this grass would perform excellently if planted wall-to-wall on a golf course. The cultivar's favorable turf grass characteristics are also shown at multitude of different heights of cut, allowing the grass to be used in all areas of a golf course (i.e. greens, tees, fairways and rough).

DETAILS OF DISCOVERY

The RJT cultivar was discovered by the Applicants on a sloping hill in an abandoned field of a sod farm located in Williston, Fla. and owned by one of the inventors of this application. The area had been planted with Tifdwarf Bermuda grass, an unpatented variety, in the spring of 1996. Soon after planting, heavy rains washed-out a nearby road, the soil and dirt from which covered the planted area. This road soil was comprised mostly of limestone dust and limestone rock, containing a high level of calcium constituents, which when wetted and then dried created a very hard crusting over the top of the newly planted turf. The area that was affected was temporarily abandoned for turf production purposes due to the turf being covered in the hard crust, thereby rendering harvesting of the turf, if even mature, near impossible.

Several growing seasons elapsed until any appreciable amount of turf grew into the above described area. The small amount of turf that did grow was kept at a very low height by constant grazing of cattle. Plans were made in the spring of 1999 to try to attempt and recover the area. During initial inspection, the Applicants noticed several areas of Bermuda grass growing, the observed grass being markedly different from what was initially planted. The grass was also markedly different from some of the other turf grasses that were still there. The Applicants originally thought that the difference in appearance between what was originally planted and the newly discovered cultivar was due to the drastic soil condition changes that occurred when the road-wash caused a high amount of calcium to be deposited over the area. That initial suspicion was negated after subsequent asexually reproduction of the new cultivar in different soils proved that the difference was still replicated. The Applicants assume at this time that the new RJT cultivar is a sexual cross between either two mutations of the original planted Tifdwarf grass or between a mutation of Tifdwarf and a common Bermuda grass growing nearby. The dwarf growth characteristics of the RJT cultivar are assumed to have evolved and sustained vigor due to constant grazing by cattle in the original grass plot.

BRIEF DESCRIPTION OF PHOTOGRAPHS

Figure 1:
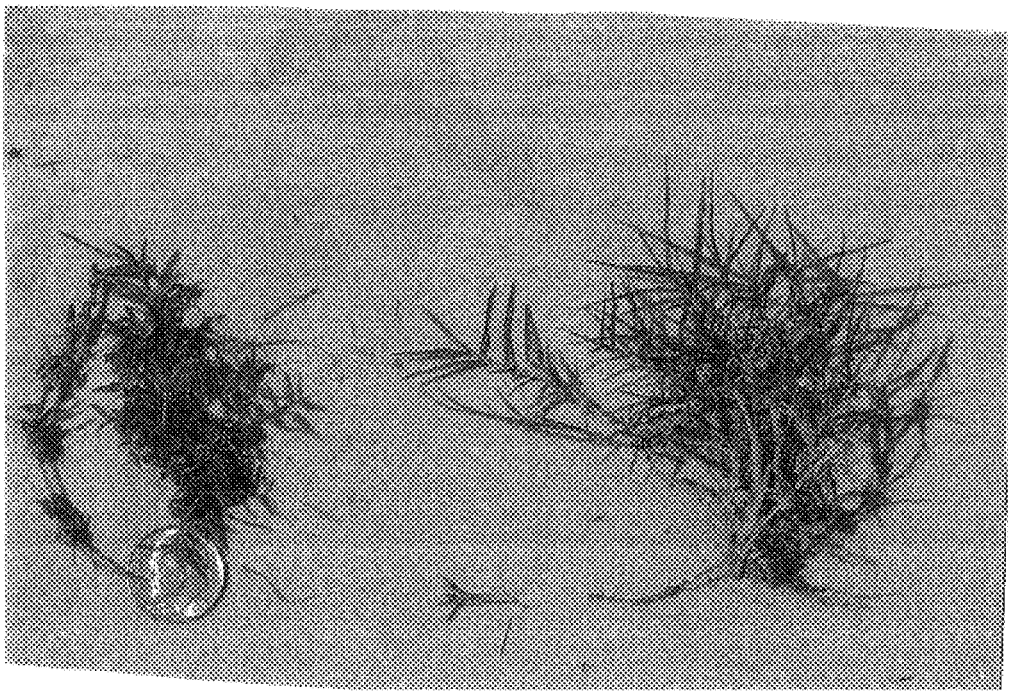
FIG. 1 is a photograph of a sprig of the RJT cultivar (on the left marked by coin) compared to a registered sprig of Tifdwarf on the right. Both varieties are at about the same age and height of cut, with the dwarf characteristic of the RJT cultivar being more pronounced compared to the Tifdwarf.
Figure 2:
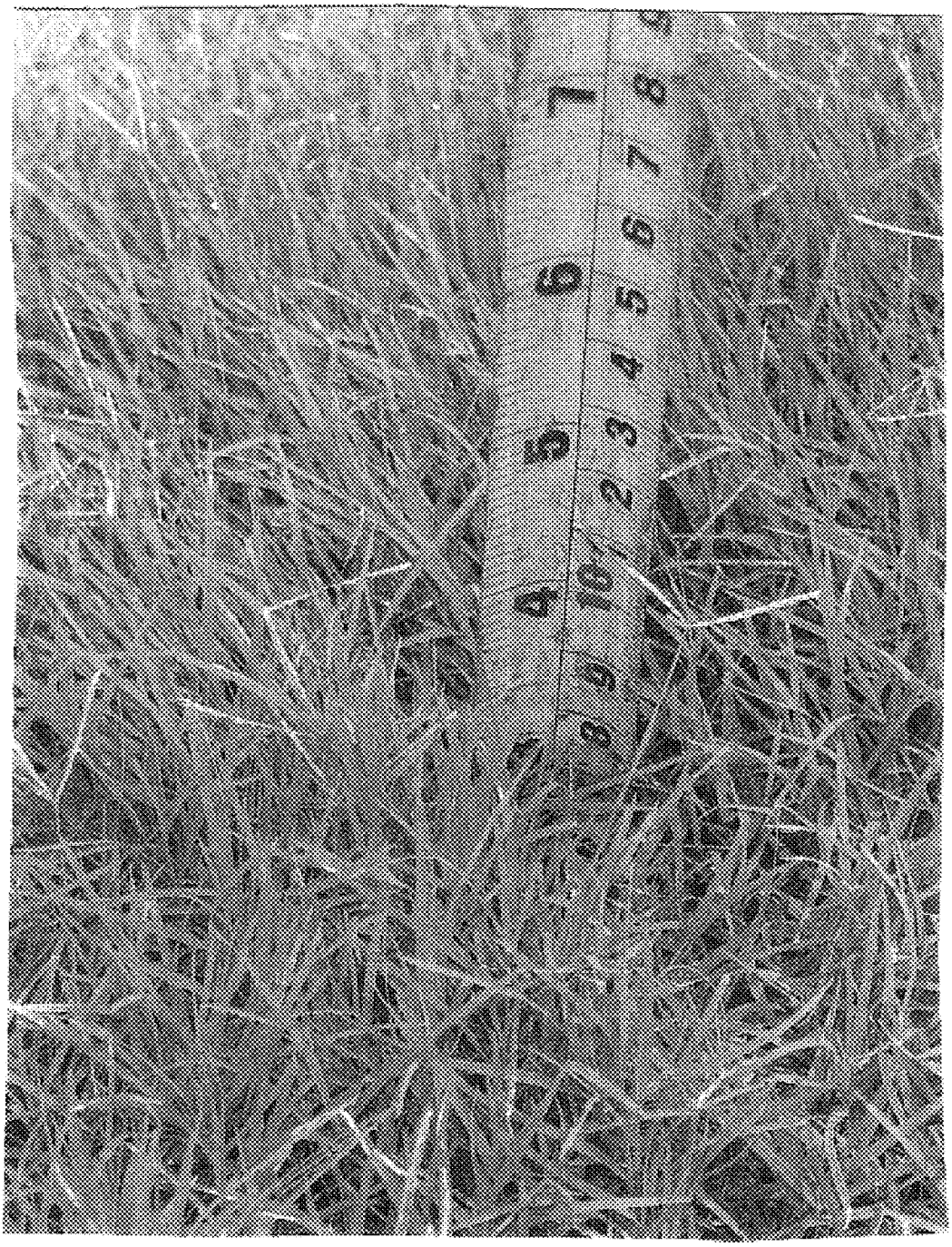
FIG. 2 is a photograph of the RJT cultivar mowed at 5 inches.
Figure 3:
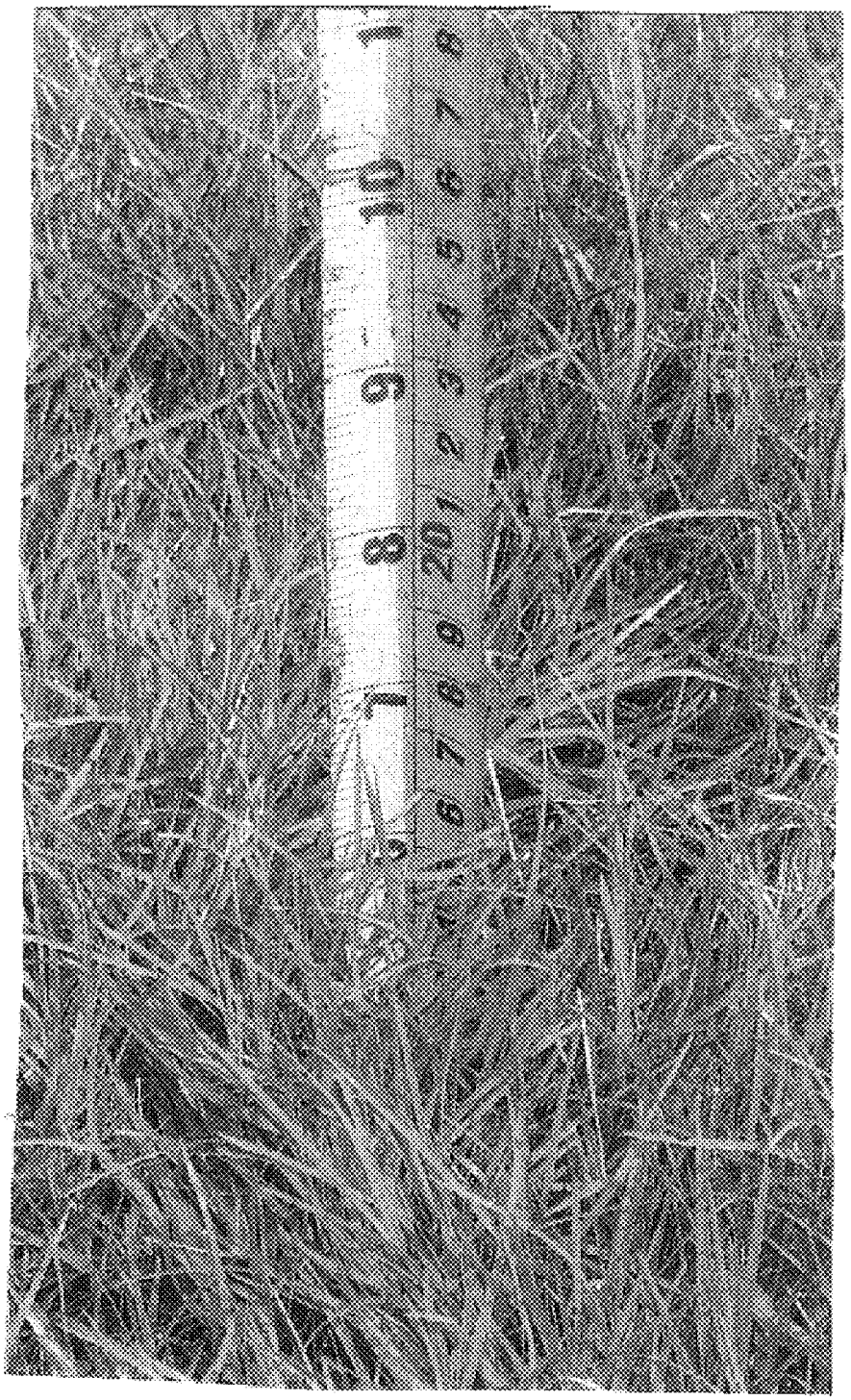
FIG. 3 is a photograph of the RJT cultivar mowed at 7 inches.
Figure 4:
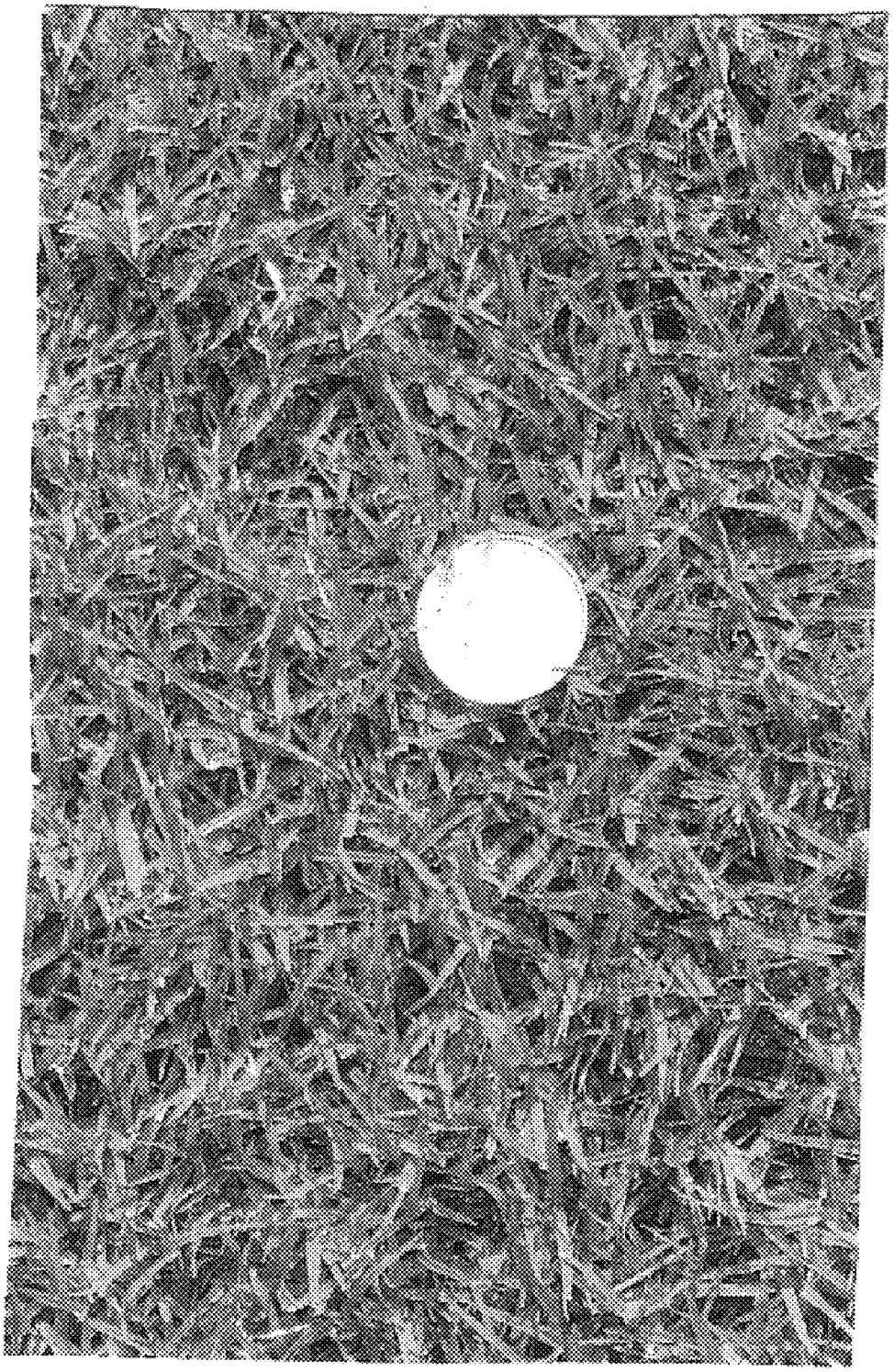
FIG. 4 is a photograph of the RJT cultivar as maintained in a normal nursery condition mown at about 0.50 inches.
Figure 5:
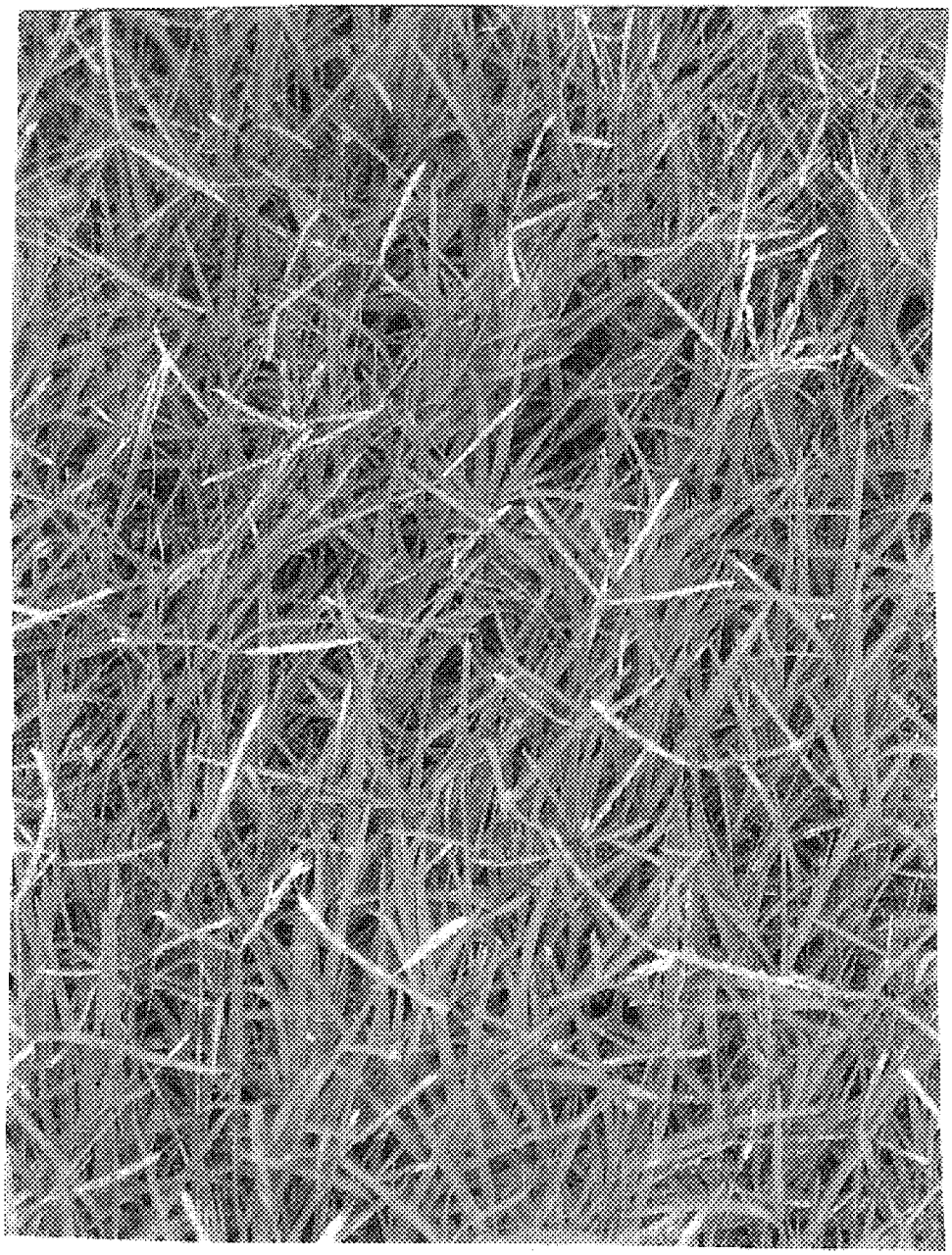
FIG. 5 is a photograph of the RJT cultivar's seed heads in nursery conditions. The seed heads are produced when under a stress such as from insect pressure.
Figure 6:
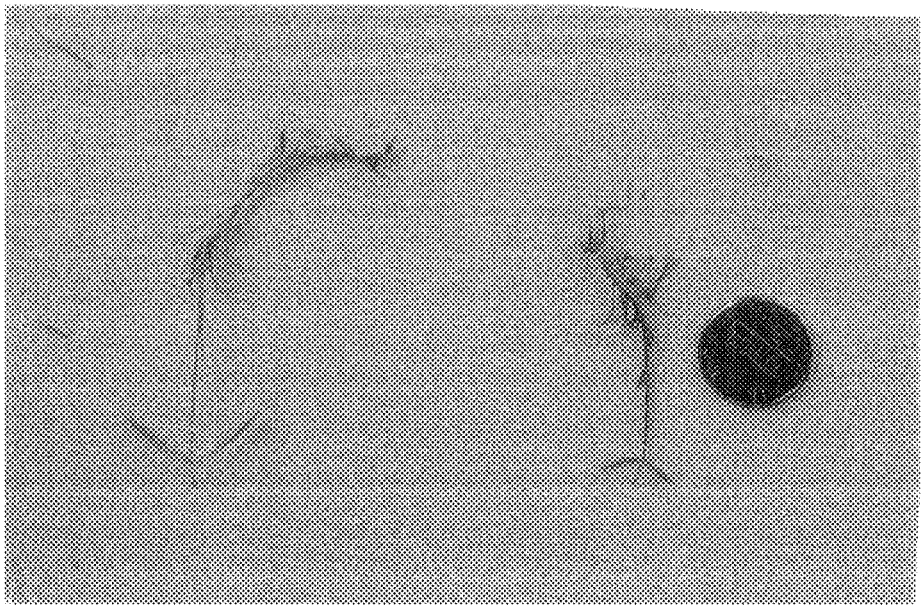
FIG. 6 is a photograph of a stolon with a seed head of the RJT cultivar (on left marked by coin) compared to a sprig with a seed head of Tifdwarf on the right.
Figure 7:
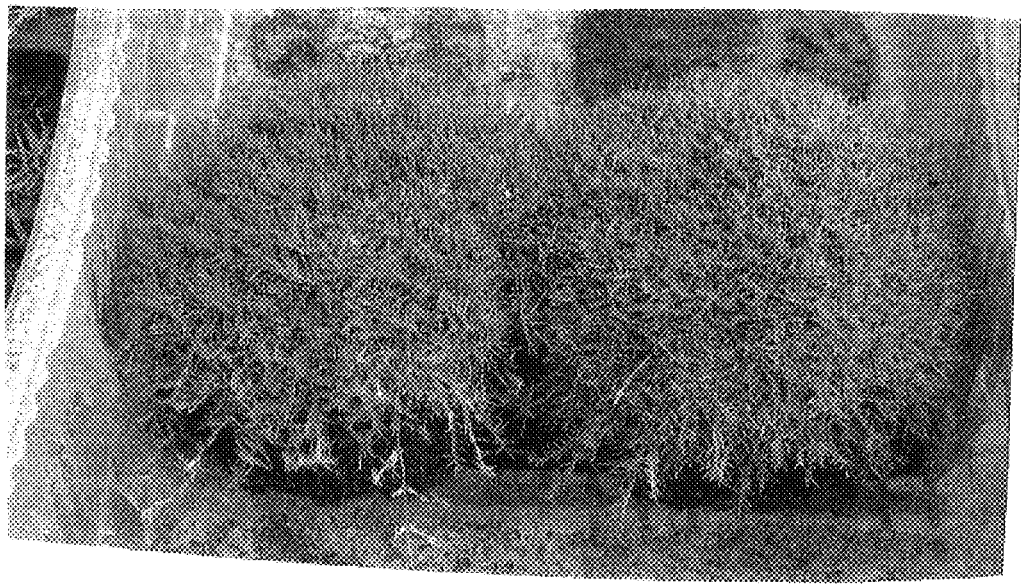

FIG. 7 is a photograph of two plugs of the RJT cultivar that were removed from the Applicant's nursery in June 2003 (the photograph was taken in June 2004). Prior to being placed in the nursery, these plugs were in a section of the outdoor nursery that did not receive any irrigation—only rainfall. The plugs were kept in a green house of one of the Applicants in a tray as shown. These two plugs never received water or any fertilizer, disease, or pest treatments while in the greenhouse for over a year. Yet the RJT grass continued to produce stolons, had reasonable green color, and excellent viability. No mutations were observed either. Several other current varieties of dwarf Bermuda grasses were treated in the same manner, but none of the varieties lasted more than two months due to total neglect.

ASEXUAL REPRODUCTION

As noted above, initial asexual reproduction confirmed that the RJT cultivar is visually different from the Tifdwarf cultivar, the closest cultivar to RJT, for reasons other than soil or chemical induced morphological responses. RJT has been asexually reproduced many times in many different soils in test plots, and has been asexually propagated on golf course putting greens that are used daily for recreational purposes. All subsequent asexual reproductions of RJT have remained true to the original cultivar type.

RJT was first asexually reproduced in test plots (nursery setting) in the summer of 1999, in Williston, Fla. Subsequent asexual reproductions have occurred in Pine Island, Fla. and Archer, Fla. Since that date, there has been no sign of mutation such as that shown by most other greens varieties of Bermuda grass, such as Tifdwarf and "ultra dwarf" Bermuda grasses such as 'Champion,' 'Classic Dwarf,' 'Tifeagle,' 'Floradwarf' and varieties. This is one aspect that will show significant differentiation between the newly discovered RJT Bermuda grass and any other presently available and patented Bermuda grasses.

Botanical description: The following is a detailed description of the new RJT cultivar based upon observation of the grass grown in field plots and under actual golf course putting green conditions on several southern U.S. golf courses and sod farms. These observations also included the RJT grown in golf course areas other than just putting greens (i.e. tees, approaches, and fairways). The RJT cultivar responds well to higher heights of cut, and therefore may be utilized in a multitude of turf grass environments. The age of the plant for the following botanical description was 24 months.

*Parentage.*—Unknown (possibly a natural mutation from Tifdwarf, or a sexual cross from two mutations of Tifdwarf, or a cross from a mutation of Tifdwarf and a natural, native occurring Bermuda grass).

*Propagation.*—Asexual (vegetative) from stolons and rhizomes.

*Growth characteristics.*—The RJT cultivar is a warm season, stoloniferous and rhizomatous perennial grass forming a thick and dense sod. Stolons or rhizomes will branch from the internodes.

*Leaf blade.*—Mostly flat, linear to deltoid shaped with the leaf base being the widest part of the leaf and tapering gradually to the leaf tip. Base of leaf blades measure approximately 1.5 mm narrowing to a total length of 5 mm approximately. These measurements were taken at a height of cut approximately at 0.25 inches. Leaf length will increase with a higher height of cut, but overall leaf width seems to remain very close to the same. Leaf tips are acute and the margins are entire. The abaxial (underside) of the leaf is rated 7.5GY 4/6 and the adaxial (top side of leaf) is rated 2.5G 4/6 both using the Munsell Color Charts for Plant Tissue. The texture of the adaxial leaf is classified as fine and more specifically as smooth with a slight waxy-like coating and glabrous. The texture of the abaxial leaf is also classified as fine, and more specifically less waxy-like than the adaxial side and nearly smooth except for minor prominence from the leaf veins, but still classified as glabrous. Both abaxial and adaxial textures were determined using a 4X band-held magnification lens.

*Stolon width.*—Average stolon width measure 1–2 mm, remaining close to the same regardless of height of cut.

*Internode length.*—Average internode length measures 4.5 mm at low heights of cut, but can increase in length at higher heights of cut.

*Sheaths.*—Compressed, loose and sparsely pubescent.

*Ligule.*—A fringe of white hairs 1 mm or less in length.

*Collar.*—Continuous, narrow, narrowing slightly at mid-vein and sparingly ciliate.

*Auricle.*—Absent.

*Inflorescence.*—Rarely produced at levels of maintenance conducive to sports field environments. Seed heads are sometimes produced under stress of insects. When seed heads are produced, only two to three digitate spikes are born, measuring approximately 1 cm or less. Spikelets are appressed in two rows on a narrow, slightly triangular rachis. Spikelet numbers are typically 3 to 5, with 3 being the most predominant. The typical spikelet length is 6 mm to 8 mm at heights cut from 0.25 inches and less. Spikelets bearing seeds are usually very low in numbers themselves. It is further believed that the few seeds produced are sterile, as sexual propagation had been attempted with no success. Moreover, no mutations, off-types, or appearances of contamination were ever observed in the nursery, field grown foundation materials, or in golf course greens over an approximately 4-year time period, giving further support to the conclusion that the seeds are sterile. Consequently, such characteristics of the present cultivar allow for excellent sod production without fear of sexual reproduction.

*Stigma and anther.*—The color of the anther is 5GY 4/6 (green to green-slight yellowish) from the Munsell color charts for plant tissue. The color of the stigma is 5RP 3/6 (purple to purple-reddish) from the Munsell color chart for tissue.

GENERAL OBSERVATIONS

The RJT cultivar has shown to be particularly well suited for use on golf course putting greens due to its aggressive growth at low heights of cut. Compared to other turf type Bermuda grasses, RJT shows favorable turf grass use at higher heights of cut also. For example, Tifdwarf, which is the closest cultivar to RJT, could become open and spindly, allowing weed invasion and an overall unfavorable appearance as a turfgrass if it were allowed to grow above 2 inches. RJT shows excellent density with a retained fine-textured leaf blade and no openness at a height of cut of 5 inches and beyond, compared to Tifdwarf. Both Tifdwarf and RJT have similar tolerances to cold temperatures, with both going off-color at the same cooler temperatures. Both cultivars have similar susceptibility to disease and insects. The leaf blade colors of both cultivars are very similar, although this can be influenced by different nutrient inputs, especially nitrogen, in both cultivars. Both cultivars have similar low-height cut tolerances, with RJT tolerating a slightly lower height than Tifdwarf.

Compared to Tifdward, RJT comes out of winter dormancy quicker (i.e. RJT "greens up" sooner) and recovers from frost and low temps more quickly than Tifdwarf. RJT has a faster rate of growth than Tifdwarf, especially horizontally with the same nutrient inputs. RJT also requires much less nitrogen to maintain its color and good high growth rates, compared to Tifdward. RJT produces much less thatch and has much better shade tolerance that Tifdwarf.

With equal, or less fertility, RJT shows a faster rate of stolon elongation with less upright growth as compared to other Bermuda grasses. Through general observations, RJT shows quicker spring green-up from winter frosts, and better color retention from prolonged cool temperatures as compared to other turf-type Bermuda grasses. The transition from winter dormancy while overseeded with cool-season grasses has also proven to be much quicker and easier as compared to other Bermuda grasses. RJT is so aggressive at the onset of warmer temperatures that it out competes the cool season grasses used for winter overseeding, and therefore has minimal difficulty during this transition period.

Disease tendencies of RJT seem to be much less than for other turf grass varieties of Bermuda. The shade tolerance of RJT has also been tested and it has proven to be much more tolerant than both Tifdwarf and Floradwarf.

The RJT cultivar has proven to be extremely adaptable to its environment compared to other green varieties of Bermuda grass. This is probably due to RJT being a natural selection as compared to some of the 'hybrid' varieties of Bermuda grass. Selection by radiation, or other sexual crosses by man tend to develop a weak turfgrass that may be susceptible to the harsh and constant-changing environmental conditions. An excellent use for RJT would be for an entity that wants a high quality putting surface, but does not to incur the large expense of a USGA green soil profile. RJT has proven that it can tolerate low mow heights coupled with compaction from foot traffic and equipment equally well in native "push-up" greens as compared to the typical USGA green.

RJT has shown that compared to other varieties of Bermuda grass used for putting greens, its overall management input (i.e. routine verticutting and topdressing) is much lower. Thatching tests were carried out in the summer of 2000 to test the RJT cultivar against other putting green Bermuda grasses. Tests proved that RJT could sustain desirable putting characteristics with fifty (50%) percent less de-thatching compared to Tifdwarf, and nearly eighty (80%) percent less de-thatching than the ultradwarf variety known as Floradwarf. The three test plots were set side by side and evaluated for the entire summer growing season of 2000 from May 1, 2000 until Oct. 31, 2000. Stimp readings were taken weekly to determine how thatch amounts would affect the speed of ball roll. All varieties of grass were mowed with a walking, reel-type hand mower at 0.125 inches. During the six-month test, RJT was verticut (de-thatched) two times, Tifdwarf was verticut four times, and Floradwarf was verticut seven times while all stimp readings from these three varieties remained approximately the same. All three varieties also had the identical nutrient input and other environmental contributing factors. This simple test showed that the RJT cultivar is a very low thatch producer compared to other types of greens-quality Bermuda grasses.

Tests on fertility also show that the RJT's vigor and overall health can be sustained with much less nutrient input, especially nitrogen. In conjunction with the above thatch tests, three separate test plots of the same three different varieties were set up to test differences in nutritional input characteristics. Once again, the plots were all mowed at 0.125 inches and received the same water, sunlight, etc. A 10-10-10 N-P-K fertilizer composition (i.e. 10% nitrogen, 10% phosphorous, and 10% potassium) was used. The Munsell Color Chart was utilized to access grass blade color and overall favorable appearance. All three plots were fertilized and the colors compared five days later. It was shown that the RJT cultivar could maintain good color and overall good visual quality for four weeks without additional fertilizer input, whereas the other two varieties needed additional fertilizer after only two weeks to sustain the same green color and favorable visual qualities.

DIVERGENT COMPARISONS TO OTHER SIMILAR VARIETIES OF BERMUDA

The four most distinguishing characteristics of the RJT cultivar as compared to any other similar turf type Bermuda grass are:

1. RJT has shown no mutation in almost four years, whereas all other Bermuda grasses of which the Applicants are familiar have been reported to have had mutations after only one to two years. This difference by itself is a valuable characteristic of the RJT cultivar, since many golf course putting greens need to be reconstructed every few years due to turf mutations.
2. The thatch production of RJT compared to other turf type dwarf Bermuda grasses is considerably lower at the same nutrient applications, with nitrogen being especially noted.
3. Overall nutrient needs are much lower for RJT, as this cultivar has proven to sustain favorable turfgrass aesthetics at fertility rates much lower than other conventional golf course Bermuda grass cultivars. In fact, after one year with absolutely no fertilizer application, the RJT cultivar was still very healthy and viable, whereas all other similar Bermuda grass cultivars had terminated long before.
4. The higher heights of cut utilized while maintaining a fine-textured leaf blade is a highly distinctive and divergent characteristic of RJT, allowing the RJT cultivar to be utilized in multiple environments.

We claim:

1. A new and distinct Bermuda grass plant, named 'RJT', as herein illustrated and described, characterized by its very fine texture when closely mown, the retention of its fine texture at higher heights of cut, its low nutrient needs, its very low thatching characteristics as compared to other dwarf Bermuda grasses, and its prolonged proven stability against mutation.

* * * * *